United States Patent
Saito

(10) Patent No.: US 11,473,057 B2
(45) Date of Patent: Oct. 18, 2022

(54) METHOD FOR OBTAINING MICROGLIA FROM PLURIPOTENT STEM CELLS

(71) Applicant: TAKARA BIO INC., Shiga (JP)

(72) Inventor: Hiroki Saito, Kusatsu (JP)

(73) Assignee: TAKARA BIO INC., Shiga (JP)

( * ) Notice: Subject to any disclaimer, the term of this patent is extended or adjusted under 35 U.S.C. 154(b) by 759 days.

(21) Appl. No.: 16/328,396

(22) PCT Filed: Sep. 1, 2017

(86) PCT No.: PCT/JP2017/031635
§ 371 (c)(1),
(2) Date: Feb. 26, 2019

(87) PCT Pub. No.: WO2018/043714
PCT Pub. Date: Mar. 8, 2018

(65) Prior Publication Data
US 2019/0194613 A1 Jun. 27, 2019

(30) Foreign Application Priority Data
Sep. 2, 2016 (JP) .............................. JP2016-171690

(51) Int. Cl.
| | | |
|---|---|---|
| C12N 15/85 | (2006.01) | |
| C12N 5/079 | (2010.01) | |
| G01N 33/50 | (2006.01) | |
| A61P 21/02 | (2006.01) | |
| A61P 25/16 | (2006.01) | |
| A61P 25/28 | (2006.01) | |
| C12N 5/0786 | (2010.01) | |

(52) U.S. Cl.
CPC ............ *C12N 5/0622* (2013.01); *A61P 21/02* (2018.01); *A61P 25/16* (2018.01); *A61P 25/28* (2018.01); *C12N 5/0645* (2013.01); *G01N 33/5058* (2013.01); *C12N 2501/165* (2013.01); *C12N 2501/22* (2013.01); *C12N 2501/2303* (2013.01); *C12N 2501/2334* (2013.01); *C12N 2502/086* (2013.01); *C12N 2502/1157* (2013.01); *C12N 2502/13* (2013.01); *C12N 2502/45* (2013.01); *C12N 2506/45* (2013.01)

(58) Field of Classification Search
None
See application file for complete search history.

(56) References Cited

U.S. PATENT DOCUMENTS

2014/0227780 A1* 8/2014 Nishino .................. A61K 35/15
435/377
2016/0186137 A1* 6/2016 Thomson ............. C12N 5/0647
435/29

FOREIGN PATENT DOCUMENTS

WO 2010/125110 11/2010

OTHER PUBLICATIONS

Sakuma et al (So No To Hattatsu, 2015, vol. 47 Supp. Supplement 1, pp. S215, E-032). (Year: 2015).*
Extended European Search Report dated Jan. 30, 2020 in corresponding European Patent Application No. 17846717.1.
Noto et al., "Development of a culture system to induce microglia-like cells from haematopoietic cells", Neuropathology and Applied Neurobiology, 2014, vol. 40, No. 6, pp. 697-713.
Notification of Reason for Refusal dated Dec. 28, 2020 in corresponding Korean Patent Application No. 10-2019-7007583, with English Machine Translation.
International Search Report dated Nov. 21, 2017 in International Application No. PCT/JP2017/031635.
International Preliminary Report on Patentability dated Mar. 14, 2019 in International Application No. PCT/JP2017/031635.
Park, J.K. et al., "Differentiation of induced pluripotent stem cells to microglia dor treatment of CNS diseases", Journal of Neurosurgery, 2013, vol. 119, p. A544, Abstract No. 628, EMBASE [online], [retrieved on Nov. 9, 2017], Retrieved from STN, Accession No. 0051184671, entire text.
Ohgidani, M. et al, "Introducing directly induced microglia-like (iMG) cells from fresh human monocytes: a novel translational research tool for psychiatric disorders", Frontiers in Cellular Neuroscience, 2015, vol. 9, Article 184, abstract.
Streit et al., "Microglia and neuroinflammation: a pathological perspective", Journal of Neuroinflammation, 2004, 1:14.
Beutner et al, "Generation of microglial cells from mouse embryonic stem cells", Nature Protocols, 2010, vol. 5, No. 9, 1481-1494.
Sullivan et al., "Induced pluripotent stem cells as a discovery tool for Alzheimer's disease", Brain Research, 2017, vol. 1656, 98-106.
Office Action dated Apr. 27, 2021 in corresponding Japanese Patent Application No. 2018-537566, with English Machine Translation, 10 pages.

* cited by examiner

*Primary Examiner* — Celine X Qian
(74) *Attorney, Agent, or Firm* — Wenderoth, Lind & Ponack, L.L.P.

(57) ABSTRACT

The purpose of the present invention is to efficiently produce microglia from pluripotent stem cells. Provided is a method for producing microglia from pluripotent stem cells, comprising the following steps: (a) a step of co-culturing a pluripotent stem cell together with a feeder cell for 7 days or longer, and obtaining a blood progenitor cell; (b) a step of co-culturing the blood progenitor cell obtained in step (a) together with a feeder cell in the presence of IL-3 and/or GM-CSF, and obtaining an embryonic monocyte; and (c) a step of, in the presence of M-CSF, co-culturing the embryonic monocyte obtained in step (b) together with an astrocyte, or culturing the embryonic monocyte using an astrocyte supernatant.

8 Claims, 3 Drawing Sheets

[Fig. 1]

[Fig. 2]
(a)
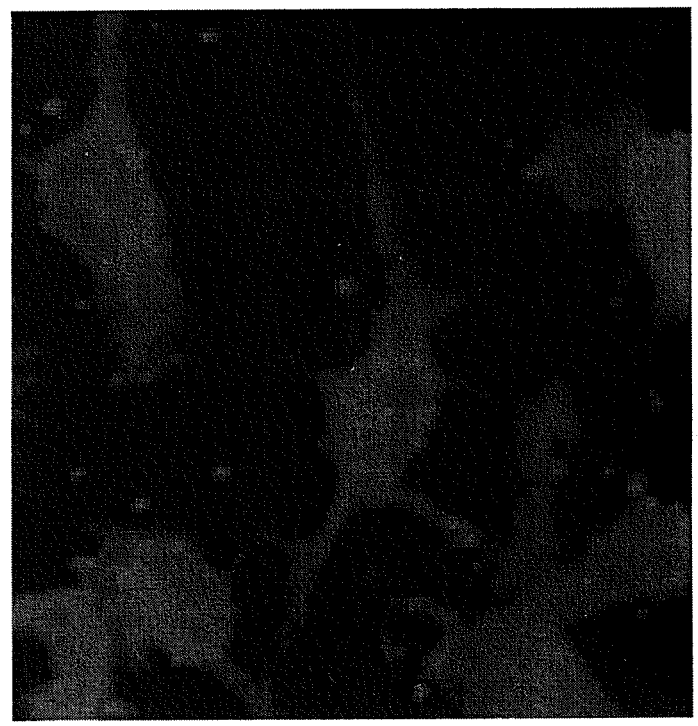
(b)

METHOD FOR OBTAINING MICROGLIA FROM PLURIPOTENT STEM CELLS

TECHNICAL FIELD

The present invention relates to a method for obtaining microglia form pluripotent stem cells.

BACKGROUND ART

Microglia are neuroglial cells present in the brain and spinal cord, and are also called Hortega cells. Microglia are derived from mesoderm. Microglia are known to be activated by invasion of foreign substances such as virus into the brain and external injury, and thereby serve various physiological functions such as sterilization and tissue repair as well as antitumor activity etc. In addition, microglia remove dead cells resulting from apoptosis or injury and waste products such as amyloid β by phagocytosis.

Regarding a relation to disease, it has been reported that microglia are involved in various diseases including chronic neurodegenerative diseases accompanied with neurodegeneration such as Alzheimer disease and Parkinson disease, and cerebral infarction, and the reactivity of microglia is changed depending on waste products accumulating in the brain which is represented by amyloid β (Non-patent Literature 1).

Therefore, it is necessary to use microglia for development and evaluation of therapeutic agents for these diseases in which microglia are involved. Thus various methods for preparing microglia have been attempted.

Non-patent Literature 2 discloses a method for obtaining microglia from mouse ES cells.

Although Patent Literature 1 discloses a method for obtaining microglia precursors from human iPS cells, Example 1 discloses that only 2-10% of cells obtained by differentiation were cells having immunoreactivity to CD45 (microglia precursors).

As described in Non-patent Literature 3, in despite of the fact that many laboratories have attempted to differentiate iPS cells into microglia, at present, a method for efficiently obtaining microglia from human iPS cells is not known.

CITATION LIST

Patent Literatures

Patent Literature 1: WO2010/125110

Non-Patent Literatures

Non-patent Literature 1: J. Neuroinflammation, Vol. 1, pp. 14 (2004)
Non-patent Literature 2: Nature Protocols, 5, 1481-1494 (2010)
Non-patent Literature 3: Brain Research, Volume 1656, Pages 98-106 (2017)

SUMMARY OF INVENTION

Problem to be Solved by the Invention

An object of the present invention is to efficiently produce microglia from pluripotent stem cells.

Solution for Problem

The inventors of the present invention intensively studied. As a result, they succeeded in efficient production of microglia based on suggestions that microglia emerge from yolk-sac macrophages in an early fetal period and migrate to central nervous system (Nature Review Immunology, 2011, 11, 775-787). Specifically, they produced microglia by culturing human iPS cells on feeder cells to prepare blood progenitor cells (step (a)), preparing monocytes from the blood progenitor cells by primitive hematopoiesis (step (b)), and co-culturing the monocytes with astrocytes (step (c)). When all the cells obtained by step (a) were subjected to step (b), all (100%) of cells were obtained as primitive monocytes. Then, when the primitive monocytes were subjected to step (c), they all (100%) differentiated into microglia. In other words, as described in Non-patent Literature 3, under the current circumstances that a method for efficiently obtaining microglia is not known, in the present invention, cells expressing a cell surface marker (Iba1) specific to microglia and macrophages, and having projections which exist not on macrophages but microglia were established very efficiently.

The inventors of the present invention further studied, and then found that it was especially preferable for increasing production efficiency that the culturing period of step (a) was for 7 days or more (especially 13 days or more), 25 ng/ml or more of IL-3 or 50 ng/ml or more of GM-CSF were added in step (b), and 25 ng/ml or more of M-SCF was added in step (c). They also found that the culturing period of step (b) did not greatly influence the production efficiency.

That is, the present invention relates to:
(1) A method for producing microglia from a pluripotent stem cell, the method comprising the following steps:
   (a) a step of co-culturing a pluripotent stem cell with a feeder cell for 7 days or more to obtain a blood progenitor cell,
   (b) a step of co-culturing the blood progenitor cell obtained by step (a) with a feeder cell in the presence of IL-3 and/or GM-CSF to obtain a primitive monocyte, and
   (c) a step of co-culturing the primitive monocyte obtained by step (b) with an astrocyte in the presence of M-CSF, or culturing the primitive monocyte obtained by step (b) using an astrocyte supernatant in the presence of M-CSF;
(2) The method according to (1), wherein the culturing period of step (a) is for 13 days or more;
(3) The method according to (1) or (2), wherein step (c) is characterized by culturing in the presence of IL-34;
(4) The method according to any one of claims 1)-(3), wherein step (b) is characterized by culturing in the presence of IL-3 and GM-CSF;
(5) The method according to any one of (1)-(4), wherein the feeder cell is a 10T1/2 cell or OP9 cell;
(6) The method according to any one of (1)-(5), wherein step (a) is characterized by culturing in the presence of VEGF;
(7) The method according to any one of (1)-(6), wherein the pluripotent stem cell is an iPS cell;
(8) The method according to (7), wherein the iPS cell is derived from human or mouse;
(9) A screening method for a preventive or therapeutic agent for disease in which microglia are involved or an improving agent for memory or learning ability, the method comprising using the microglia produced by the method according to any one of (1)-(8);
(10) The screening method according to (9), wherein the disease in which microglia are involved is trauma of spinal cord, neuropathy caused by cerebral stroke, epilepsy, neuropathic pain, vascular occlusive eye disease, demyelinating disease, psychiatric disease, cerebral infarction, Nasu-Hakola disease, or neurodegenerative disease;

(11) The screening method according to (10), wherein the neurodegenerative disease is Alzheimer disease, Parkinson disease, or amyotrophic lateral sclerosis.

Effects of the Invention

According to the method of the present invention, microglia can be efficiently produced from pluripotent stem cells. The microglia thus obtained can be used for various basic studies including study of microglia itself and study for diseases that microglia are involved in. Further, the microglia are extremely useful in a method for screening therapeutic agents for diseases that microglia are involved in, wherein the method comprises using microglia, or in selecting so-called tailor-made therapeutic agents, in which therapeutic agents best suited to patients are selected by using microglia prepared from pluripotent stem cells established from the individual patients. Application of the microglia to cell therapy is also expected.

BRIEF DESCRIPTION OF DRAWINGS

FIG. 1 is an Iba1 immunostaining image of cells after differentiation induction by the method of the present invention.
FIG. 2 Both FIGS. 2 (a) and (b) are magnified images of cells after differentiation induction by the method of the present invention.

MODE FOR CARRYING OUT THE INVENTION

Figure 3:
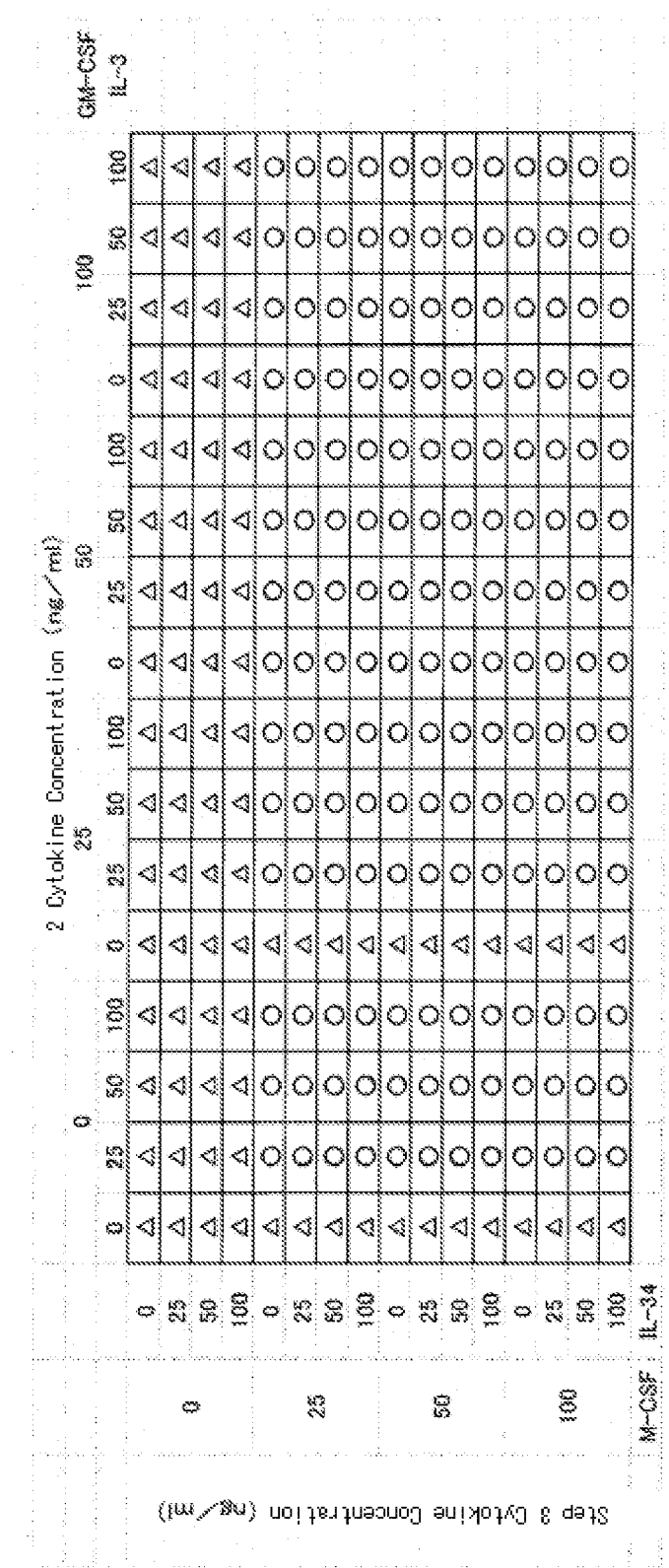
FIG. 3 shows the results of the Iba1 immunostaining performed in Example 5.

Terms as used herein have usual meanings in the field, unless otherwise specified. Au used herein, techniques such as molecular biological techniques and immunological techniques are performed by known methods, unless otherwise specified.

I. Method for Differentiation Induction into Microglia from Pluripotent Stem Cells The method for differentiation induction into microglia from a pluripotent stem cell of the present invention comprises the following steps:
(a) a step of co-culturing a pluripotent stem cell with a feeder cell for 7 days or more to obtain a blood progenitor cell,
(b) a step of co-culturing the blood progenitor cell obtained by step (a) with a feeder cell in the presence of IL-3 and/or GM-CSF to obtain a primitive monocyte, and
(c) a step of co-culturing the primitive monocyte obtained by step (b) with an astrocyte in the presence of M-CSF, or culturing the primitive monocyte obtained by step (b) using an astrocyte supernatant in the presence of M-CSF.

Specifically, in step (a), a pluripotent stem cell is cultured under suitable conditions for promoting differentiation into a blood progenitor cell. The "suitable conditions for promoting differentiation into a blood progenitor cell" mean co-culturing the pluripotent stem cell with a feeder cell.

The term "pluripotent stem cell(s)" means cells keeping undifferentiated and keeping pluripotency, which are represented by embryonic stem cells (ES cells) or induced pluripotent stem cells (iPS cells). The ES cells may be ES cells generated by nuclear reprogramming of somatic cells. Examples of pluripotent stem cells other than ES cells include embryonic germ cells (EG cells) which are derived from primordial germ cells, multipotent germline stem cells (mGS cells) which are isolated from testes, and multipotent adult progenitor cells (MAPCs) which are isolated from bone marrow. In the present invention, the pluripotent stem cells are from human. In the present invention, the pluripotent stem cells are preferably iPS cells, more preferably human iPS (hiPS) cells.

The pluripotent stem cells can be prepared by known methods. The known methods are described specifically in WO2007/069666, WO2010/068955, WO2011/030915, WO2013/094771, WO2014/014119, and WO2014/065435.

Regarding human iPS cell lines, for example, TkDA3-4 is available from Tokyo University Stem Cell Bank, and 201B7 is available from the Center for iPS Cell Research and Application, Kyoto University.

Regarding human ES cell lines, for example, WA01(H1) and WA09(H9) are available from WiCell Research Institute, and KhES-1, KhES-2 and KhES-3 are available from Institute for Frontier Medical Sciences, Kyoto University.

When an ES cell or iPS cell is used as the pluripotent stem cell, for example, IMDM supplemented with FBS at final concentration of 15% is used as a medium. Even when a serum-free medium is used, a growth factor, a supplement or the like may be added to the medium as appropriate. VEGF may be added to a medium. In the case of culturing under low-oxygen conditions, however, an effect equivalent to that when VEGF is added to a medium can be obtained without adding VEGF.

The concentration of VEGF is not particularly limited as long as a blood progenitor cell is obtained. The concentration of VEGF may be 5 ng/ml to 50 ng/ml, preferably 20 ng/ml or more.

The term "low-oxygen conditions" means that the oxygen concentration in atmosphere for culturing cells is significantly lower than the oxygen concentration in the air. Specifically, the low-oxygen conditions include conditions wherein the oxygen concentration is lower than oxygen concentration in 5-10% $CO_2$/95-90% air atmosphere which is generally used for usual cell culture, and examples of such conditions include conditions wherein the oxygen concentration in atmosphere is 18% or less. The oxygen concentration in atmosphere is preferably 15% or less (e.g., 14% or less, 13% or less, 12% or less, 11% or less, etc.), 10% or less (e.g., 9% or less, 8% or less, 7% or less, 6% or less, etc.), or 5% or less (e.g., 4% or less, 3% or less, 2% or less, etc.). The oxygen concentration in atmosphere is also preferably 0.1% or more (e.g., 0.2% or more, 0.3% or more, 0.4% or more, etc.), 0.5% or more (e.g., 0.6% or more, 0.7% or more, 0.8% or more, 0.9% or more, etc.), or 1% or more (e.g., 1.1% or more, 1.2% or more, 1.3% or more, 1.4% or more, etc.).

A means for creating low-oxygen conditions in cellular environment is not particularly limited. A preferable example thereof is a method comprising culturing a cell in a $CO_2$ incubator capable of controlling the oxygen concentration, which is the easiest means. The $CO_2$ incubator capable of controlling the oxygen concentration is commercially available from various device manufacturers (for example, $CO_2$ incubators for low-oxygen culturing produced by manufacturers such as Thermo scientific, Ikemoto Scientific Technology Co., Ltd., Juji-field co. JP, WAKENYAKU CO., LTD., and the like can be used).

The "feeder cell" may be any cell that contributes to differentiation induction of a pluripotent stem cell. For example, a mouse embryo fibroblast, preferably a 10T1/2 cell line, an OP9 cell or the like can be used as the feeder cell. When the feeder cell is used, it is preferable to suppress the cell growth by irradiation or the like.

A culturing period is not particularly limited as long as it is a period of enough days for the pluripotent stem cell to "differentiate into a blood progenitor cell". Examples of the culturing period include, but not limited to, a period of 7 days or more, a period of 10 days or more, and a period of 13 days or more. A person skilled in the art can appropriately adjust the culturing period depending on the conditions used.

Other culturing conditions include, but not limited to, for example 5% $CO_2$, 36-38° C., preferably 37° C. Culturing under the above-mentioned conditions can be performed using, for example, a known $CO_2$ incubator.

The term "blood progenitor cell(s)" means hematopoietic cells characterized by a single marker or a combination of plural markers selected from the group consisting of CD34 negative cells, CD34 positive cells, Lin negative cells (CD2 negative cells, CD3 negative cells, CD4 negative cells, CD7 negative cells, CD8 negative cells, CD10 negative cells, CD14 negative cells, CD16 negative cells, CD19 negative cells, CD20 negative cells, CD24 negative cells, CD41 negative cells, CD45 negative cells, CD56 negative cells, CD66b negative cells, or CD235a negative cells), CD38 negative cells, CD90 positive cells, CD49f positive cells, VEGFR2 positive cells, CD31 positive cells, CD43 positive cells, CD34 positive and CD45 positive cells, Rhodamine weakly-positive cells, or Hoechst negative/weakly-positive cells.

In step (b), the blood progenitor cell obtained by step (a) is cultured under suitable conditions for promoting differentiation into a primitive monocyte (primitive hematopoiesis occurs). The "suitable conditions for promoting differentiation into a primitive monocyte" means co-culturing the blood progenitor cell with the feeder cell. Specifically, for example, the blood progenitor cell and the feeder cell are co-cultured in the presence of IL-3 and/or GM-CSF.

The concentration of IL-3 and GM-CSF is not particularly limited as long as a primitive monocyte is obtained. For example, the concentration of IL-3 may be 1 ng/ml to 200 ng/ml, 20 ng/ml to 150 ng/ml, or 25 ng/ml to 100 ng/ml. The concentration of GM-CSF may be 1 ng/ml to 200 ng/ml, 20 ng/ml to 150 ng/ml, or 25 ng/ml to 100 ng/ml. For efficient production, the concentration of IL-3 is particularly preferably 25 ng/ml or more, and the concentration of GM-CSF is particularly preferably 50 ng/ml or more.

A culturing period is not particularly limited as long as it is a period of days enough for "differentiation into a primitive monocyte" and capable of primitive hematopoiesis. A person skilled in the art can appropriately adjust the culturing period depending on the conditions used.

Other culturing conditions are the same as those for step (a) described above.

The term "monocyte(s)" means cells characterized by a single marker or a combination of plural markers selected from the group consisting of CD11b positive cells, CD14 positive cells, CD15 positive cells, CD4 positive cells, CD163 positive cells, CD9 positive cells, CD11c positive cells, CDw12 positive cells, CD13 positive cells, CD17 positive cells, CD31 positive cells, CD32 positive cells, CD33 positive cells, CD35 positive cells, CD36 positive cells, CD38 positive cells, CD40 positive cells, CD43 positive cells, CD45RO positive cells, CD45RA positive cells, CD45RB positive cells, CD49b positive cells, CD49e positive cells, CD49f positive cells, CD63 positive cells, CD64 positive cells, CD65s positive cells, CD68 positive cells, CD74 positive cells, CD84 positive cells, CD85 positive cells, CD86 positive cells, CD87 positive cells, CD89 positive cells, CD91 positive cells, CD92 positive cells, CD93 positive cells, CD98 positive cells, CD101 positive cells, CD102 positive cells, CD111 positive cells, CD112 positive cells, CD115 positive cells, CD116 positive cells, CD119 positive cells, CD121b positive cells, CD123 positive cells, CD127 positive cells, CD128b positive cells, CD131 positive cells, CD142 positive cells, CD147 positive cells, CD147 positive cells, CD156a positive cells, CD155 positive cells, CD157 positive cells, CD162 positive cells, CD163 positive cells, CD164 positive cells, CD168 positive cells, CD170 positive cells, CD171 positive cells, CD172a positive cells, CD172b positive cells, CD180 positive cells, CD184 positive cells, CD191 positive cells, CD192 positive cells, CD195 positive cells, CDw198 positive cells, CD206 positive cells, CDw210 positive cells, CD213a1 positive cells, CD213a2 positive cells, CD226 positive cells, CD277 positive cells, CD281 positive cells, CD282 positive cells, CD284 positive cells, CD295 positive cells, CD300a positive cells, CD300c positive cells, CD300e positive cells, CD302 positive cells, CD305 positive cells, CD312 positive cells, CD317 positive cells, CD322 positive cells, CD328 positive cells, or CD329 positive cells.

The term "primitive hematopoiesis" originally means hematopoiesis that transiently occurs in yolk-sac in an early fetal period. In the present specification, that the hematopoietic stage is "primitive" can be confirmed, for example, by using a method as described in step 2 in Example 1(5).

In step (c), the primitive monocyte obtained by step (b) is cultured under suitable conditions for promoting differentiation into microglia. The "suitable conditions for promoting differentiation into microglia" means co-culturing the primitive monocyte with an astrocyte, or culturing the primitive monocyte using an astrocyte supernatant. Specifically, for example, the primitive monocyte and an astrocyte are co-cultured in the presence of M-CSF, or the primitive monocyte is cultured using an astrocyte supernatant in the presence of M-CSF. In addition, IL-34 may be present.

The concentration of IL-34 and/or M-CSF is not particularly limited as long as microglia are obtained. For example, the concentration of IL-34 may be 1 ng/ml to 200 ng/ml, 20 ng/ml to 150 ng/ml, or 25 ng/ml to 100 ng/ml. The concentration of M-CSF may be 1 ng/ml to 200 ng/ml, 20 ng/ml to 150 ng/ml, or 25 ng/ml to 100 ng/ml. M-CSF greatly influences efficient production of microglia, and the concentration of M-CSF is particularly preferably 25 ng/ml or more.

The "astrocyte supernatant" is obtained by culturing an astrocyte obtained from nerve tissue in a nutritive medium. For example, the astrocyte supernatant can be prepared according to a method described in WO2006/028049.

A culturing period is not particularly limited as long as it is a period of days enough for "differentiation into microglia". Examples of the culturing period include, but not limited to, a period of 3 days or more, a period of 5 days or more, a period of 7 days or more, and a period of 8 days or more. A period of 7 days or more is particularly preferred. A person skilled in the art can appropriately adjust the culturing period depending on the conditions used.

Other culturing conditions are the same as those for step (a) described above.

That the cell thus obtained is "microglia" can be confirmed by using a known index. For example, the "microglia" are cells characterized by a single marker or a combination of plural markers selected from the group consisting of Iba1 positive cells, CD11b positive cells, P2Y12 positive cells, P2X7 positive cells, P2X4 positive cells, IL-1β positive cells, CX3CR1 positive cells, CCR2 positive cells, CCR7 positive cells, CD80 positive cells, CD209 positive cells, CD23 positive cells, CD163 positive cells, TREM2 positive cells, CD45 positive cells, P2X2 positive cells, CCL21 positive cells, IRF8 positive cells, IRF5 positive cells, TLR-4 positive cells, OX42 positive cells, CD14 positive cells, CD16 positive cells, integrin-α4 positive cells, integrin-β1 positive cells, or CD68 positive cells.

Among the above-mentioned markers, for example, Iba1 positive cells, CD11b positive cells and the like are expressed not only in microglia but also in macrophages. For example, microglia can be distinguished from macrophages by combining the markers with any of the following characteristics.

Shape (projections) characteristic of microglia
Expression of P2Y12 which is a purinergic receptor In the present invention, unless otherwise specified, the medium may be prepared as a basal medium. Examples of the basal medium include an IMDM medium, a 199 medium, an Eagle's minimal essential medium (EMEM), an alpha-MEM medium, a Dulbecco's modified Eagle's medium (DMEM), a Ham's F12 medium, an RPMI1640 medium, a Fischer's medium, a Glasgow MEM, and a mixture thereof. The basal medium may contain serum or a cytokine.

In the case of adherent cell culture, for the purpose of improving the adhesive property of cells, the surface of a culture dish may be coated with a cell support substrate such as collagen I, collagen IV, gelatin, poly-L-lysine, poly-D-lysine, laminin, fibronectin, or matrigel TM (manufactured by Becton, Dickinson and Company).

The cytokine used in the present invention such as VEGF, IL-3, IL-34, M-CSF, or GM-CSF may be a native cytokine, or a recombinant cytokine prepared by gene engineering. As used herein, the cytokine does not have to be full length, and may be a partial protein or peptide containing a region related to binding with a receptor. The protein or peptide may be altered in its amino acid sequence or steric structure as long as the receptor-binding ability is not lost. Further, the cytokine used in the present invention may be a protein or peptide or drug capable of functioning as an agonist for the receptor of the cytokine.

II. Screening Method (Screening Method for Therapeutic Agent for Disease that Activation of Microglia is Involved in)

The present invention provides a screening method for a substance that acts on microglia, comprising contacting the microglia obtained by above I with a test substance.

The "test substance" may be any known compound or a novel compound. Examples of the test substance include nucleic acid, sugar, lipid, protein, peptides, organic low-molecular compounds, compound libraries prepared using combinatorial chemistry techniques, random peptide libraries prepared by solid-phase synthesis or phage display, and natural ingredients derived from microorganisms, animals, plants, marine organisms, and the like.

In the screening method, the microglia obtained by above I is brought into contact with the test substance, and then, degrees of effects of the test substance on the microglia (e.g., shape changes, production and release of cytokines, phagocytosis, etc.) are determined. The degrees are compared with the case where the microglia are not contacted with the test substance. Then, the test substance that remarkably changes the degrees of effects as compared with the case where the microglia are not contacted with the test substance is selected as an effective constituent.

As a determination method, a known method in the field can be used. For example, the shape change of microglia can be determined by imaging of the microglia and image processing. The concentration of a cytokine released into a culture supernatant can be determined by an ELISA method. An act of phagocytizing beads can be quantified by image processing.

The test substance thus screened may be used as a preventive or therapeutic agent for trauma of spinal cord, neuropathy caused by cerebral stroke, epilepsy, neuropathic pain, vascular occlusive eye disease, demyelinating disease (multiple sclerosis, Guillain-Barr syndrome, etc.), psychiatric disease (depression, schizophrenia, autism, developmental disability, dependence, etc.), cerebral infarction, Nasu-Hakola disease, or neurodegenerative disease (in particular, Alzheimer disease, Parkinson disease, amyotrophic lateral sclerosis, etc.) and the like, or an improving agent for memory or learning ability.

(Method for Screening Tailor-Made Therapeutic Agent)

As used herein, the term "tailor-made therapeutic agent(s)" means therapeutic agents best suited to the properties of individual patients.

The present invention provides a screening method for a therapeutic agent that acts on microglia, comprising bringing the microglia obtained by differentiation induction of a induced pluripotent stem cell prepared from a somatic cell of a subject suffering from trauma of spinal cord, neuropathy caused by cerebral stroke, epilepsy, neuropathic pain, vascular occlusive eye disease or neurodegenerative disease into contact with a known therapeutic agent. The therapeutic agent thus screened can be a therapeutic agent best suited to the subject from which the induced pluripotent stem cell has been established.

Examples of the known therapeutic agent used in the present invention include, but not limited to, therapeutic agents for trauma of spinal cord such as baclofen and tizanidine, therapeutic agents for epilepsy such as Phenytoin, Phenobarbital, Carbamazepine, valproic acid, ethosuximide, zonisamide, gabapentin, topiramate, lamotrigine, and levetiracetam, therapeutic agents for neuropathic pain such as pregabalin, therapeutic agents for Alzheimer disease such as donepezil, rivastigmine, galantamine, and memantine.

EXAMPLES

Hereinafter, the present invention is further explained in detail by means of Examples which the present invention is not limited to.

Example 1 Production of Microglia (1) Feeder Cell (Mouse Embryonic Fibroblast; MEF)

A fetus (E13.5) of a mouse (line; ICR) was anatomized under a stereomicroscope, and after blood removal, the head, limbs and internal organs were removed. The remaining parts were cuts into small pieces with scissors, and then mixed with 10 ml/fetus of a digestive solution [0.05% trypsin-ethylenediamine tetra acetic acid (EDTA) (manufactured by Invitrogen)+1/1000 recombinant DNase (manufactured by TAKARA BIO INC.)]. The mixture was stirred at room temperature for about an hour with a stirrer to let the small pieces disperse. To the mixture was added an equal amount of medium A [D-MEM (manufactured by Sigma)+ 10% fetal bovine serum (FBS) (manufactured by Equitech-Bio)+1/100 penicillin-streptomycin (manufactured by Invitrogen)] to stop the enzymatic reaction. A cell dispersion was collected through a cell strainer (700; manufactured by BD Falcon), and centrifuged (300G, 3 minutes) to remove a supernatant. A pellet was resuspended in medium A, and the number of cells was counted. Then, the cells were seeded at $4\times10^6$ cells/flask in a flask (150 cm$^2$; manufactured by TPP)

that had been coated with 0.1% gelatin (manufactured by Sigma)/phosphate buffered saline (PBS) (manufactured by wako) for 30 minutes. After culturing for 3 days, the cells were washed with PBS and then dissociated by adding 0.05% trypsin-EDTA. An equal amount of medium A was added to stop the enzymatic reaction. A cell dispersion was collected and centrifuged to obtain a pellet. The pellet was suspended in CELLBANKER 1 (manufactured by Nippon Zenyaku Kogyo Co., Ltd.) and cryopreserved. Then, the cryopreserved cells were thawed and seeded at $2 \times 10^6$ cells/flask in a flask that had been coated with gelatin in the same manner as described above. After culturing for 3 days, the cells were dissociated in the same manner as described above, and seeded at $2 \times 10^6$ cells/flask in a fresh flask that had been coated with gelatin in the same manner as described above. After culturing for 3 days, the medium in the flask was exchanged with medium A supplemented with 10 μg/ml mitomycin C (MMC; manufactured by Sigma) to stop the cell growth. After culturing for 90 minutes, the cells were washed with PBS, and then dissociated in the same manner as described above. The cells thus obtained were cryopreserved in the same manner as described above. The cryopreserved MEF that had been treated with MMC was thawed on the day before use, and seeded at $5 \times 10^5$ cells/dish on a 10 cm gelatin-coated cell culture dish.

(2) hiPS Cell

Cell line TkDA3-4 purchased from Tokyo University Stem Cell Bank and cell line 201B7 purchased from the Center for iPS Cell Research and Application, Kyoto University were used.

MEF prepared by the method described in (1) was used as a feeder cell. DMEM (manufactured by Invitrogen)+20% KnockOut Serum Replacement (KSR) (manufactured by Gibco)+1/100 penicillin/streptomycin (manufactured by Invitrogen) was used as a medium. Dissociation Solution (manufactured by ReproCELL) was used as a cell dissociation solution.

(3) Stromal Cell (10T1/2)

Stromal cell 10T1/2 was purchased from Riken BioResource Research Center.

BME (manufactured by Invitrogen)+10% fetal calf serum (FCS) (manufactured by Hyclone)+1/100 GlutaMAX1 (manufactured by Invitrogen)+1/100 penicillin/streptomycin (manufactured by Invitrogen) was used as a medium. As a cell dissociation solution, 0.05% trypsin-EDTA (manufactured by Invitrogen) was used. The cells were maintained in a 150 cm² flask by subculture twice a week. The cells were subcultured at about 1/8-fold cell density (the cells in one flask were subcultured into about 8 flasks) every time (the cell density was maintained within a range of $5 \times 10^5$ to $5 \times 10^6$ cells/flask). The cells up to passage number p30 were treated with MMC to inhibit the cell growth, and then used. The MMC-treated 10T1/2 was seeded on a 10 cm gelatin-coated cell culture dish at $1 \times 10^6$ cells/dish.

(4) Primary Cultured Rat Astrocyte

A cerebrum was separated from a newborn fetus (P5-7), and meninges were peeled off by using tweezers. The brain was mechanically destroyed and dispersed by adding medium B [AdDMEM/F12 (manufactured by Invitrogen)+10% fetal calf serum (FCS) (manufactured by Hyclone)+1/100 GlutaMAX1 (manufactured by Invitrogen)+1/100 penicillin/streptomycin (manufactured by Invitrogen)] and pipetting. After still standing, a supernatant was collected, subjected to a cell strainer (100Φ; manufactured by BD Falcon), and centrifuged (200G, 4 minutes) to obtain a pellet. The cells thus obtained were resuspended in medium B. After counting, the cells were seeded at $5 \times 10^5$ cells/flask in a poly-D-lysine (PDL)-coated flask (75 cm²; manufactured by BD). Two days and 5 days after seeding, the medium B was exchanged with new one (after the flask was shaken by a shaker for 3 hours), and the cells were cultured for 7 days, and then used. The cells were shaken by a shaker for 3 hours before collection, and after the medium B was exchanged with PBS, the cells were further shaken for 5 hours. After removal of PBS, 0.25% trypsin-EDTA (manufactured by nacalai tesque) was added to the cells. After the cells were shaken by a shaker for 3 minutes, an equal amount of medium B was added to stop the enzymatic reaction, and then the cells were collected. The cells thus obtained were centrifuged (300G for 3 minutes) to obtain a pellet. The pellet was cryopreserved in a CELLBANKER. The cryopreserved astrocytes were thawed and seeded on a 10 cm gelatin-coated cell culture dish at $2.5 \times 10^5$ cells/dish. After 4 days, the medium B was exchanged with new one, and on day 7, the medium B was exchanged with medium C for co-culturing [DMEM (manufactured by Invitrogen)+10% FCS (manufactured by Hyclone)+1/100 GlutaMAX1 (manufactured by Invitrogen)+1/100 sodium pyruvate (manufactured by Invitrogen)+1/100 HEPES (manufactured by Invitrogen)+1/100 penicillin/streptomycin (manufactured by Invitrogen)]. After culturing for 3 hours, the cells were used.

(5) Differentiation Induction

Step 1

A 10 cm cell culture dish attaching hiPS cells that had been subcultured by the method described in (2) was washed with PBS. To the dish was added 1.5 ml of Dissociation Solution (manufactured by ReproCELL) to dissociate MEF while the dish was swung. The dissociated MEF was aspirated with an aspirator, and further washed with PBS. After adding 10 ml of differentiation medium D [IMDM (manufactured by Invitrogen)+15% fetal calf serum (FCS) (manufactured by EquitechLab)+1/100 GlutaMAX1 (manufactured by Invitrogen)+1/100 ITS-X (manufactured by Invitrogen)+0.5 mmol/l monothioglycerol (manufactured by wako)+50 μg/ml L-ascorbic acid phosphate magnesium salt n-hydrate (manufactured by wako)+1/100 penicillin/streptomycin (manufactured by Invitrogen)], the hiPS cells were scraped with a cell scraper. The hiPS cells thus obtained were seeded at a density of 1/40 (the cells on one dish were seeded on about 40 dishes) on the 10T1/2 cells that had been subcultured by the method described in (3), together with 20 ng/ml of VEGF (manufactured by PEPROTECH; according to Non-patent Literature 4: Blood 2008 111: 5298-5306, it is not necessary to add VEGF). After 3, 6, 8, 10 and 12 days from seeding, the medium was exchanged with differentiation medium E [IMDM (manufactured by Invitrogen)+15% fetal calf serum (FCS) (manufactured by EquitechLab)+1/100 GlutaMAX1 (manufactured by Invitrogen)+1/100 ITS-G (manufactured by Invitrogen)+0.5 mmol/l monothioglycerol (manufactured by wako)+50 μg/ml L-ascorbic acid phosphate magnesium salt n-hydrate (manufactured by wako)+1/100 penicillin/streptomycin (manufactured by Invitrogen)] supplemented with 20 ng/ml of VEGF (manufactured by PEPROTECH; according to Non-patent Literature 4, it is not necessary to add VEGF). On day 13, the cells were collected. The cells were scraped from the cell culture dish with a cell scraper while Sac was destroyed, and then the cells were collected through a cell strainer (40Φ). After centrifugation [120G (it was confirmed that centrifugation at 100-150G did not affect a recovery rate and purity), 10 minutes, no brake], a pellet was resuspended in differentiation medium E. Since about 50% of the cells thus obtained were CD34-positive, it was found that blood progenitor cells were prepared.

Step 2

The blood progenitor cells obtained by step 1 were cultured on 10T1/2 together with 50 ng/ml of erythropoietin (manufactured by PEPROTECH) to obtain erythrocytes. Since the hemoglobin type of the erythrocytes was fetal-type hemoglobin up to day 6, it was found that only primitive hematopoiesis was induced up to day 6 of differentiation induction from the blood progenitor cells.

To the all cells obtained by step 1 were added 50 ng/ml of IL-3 (manufactured by PEPROTECH) and 50 ng/ml of GM-CSF (manufactured by PEPROTECH), and resuspension of 5 cell culture dishes was seeded on 10T1/2 in one cell culture dish. After 3 days, 5 ml of differentiation medium E containing 50 ng/ml of IL-3 and 50 ng/ml of GM-CSF was added to the cells. After 6 days, the cells were collected by pipetting. The cell suspension thus obtained was centrifuged (300G, 3 minutes) to obtain a pellet. Since all (100%) cells of the pellet were CD14-positive, these cells were regarded as primitive monocytes taking the primitive hematopoiesis up to day 6 into consideration.

Step 3

The primitive monocytes obtained by step 2 were resuspended in medium F for co-culturing [DMEM (manufactured by Invitrogen)+10% FCS (manufactured by EquitechLab)+1/100 GlutaMAX1 (manufactured by Invitrogen)+1/100 sodium pyruvate (manufactured by Invitrogen)+1/100 HEPES (manufactured by Invitrogen)+1/100 penicillin/streptomycin (manufactured by Invitrogen)]. To the suspension were added 50 ng/ml of M-CSF (manufactured by PEPROTECH) and 50 ng/ml of IL-34 (manufactured by PEPROTECH), and the cells were seeded at a density of 1/2 on the primary cultured rat astrocytes described in (4). Two days after seeding, 5 ml of medium F supplemented with 50 ng/ml of M-CSF and 50 ng/ml of IL-34 was added. On day and day 7, 7 ml of the medium was collected and centrifuged (300 G, 3 minutes). A pellet was resuspended in 8 ml of medium F supplemented with 50 ng/ml of M-CSF, 50 ng/ml of IL-34, and 50 ng/ml of TGF-β1 (manufactured by PEPROTECH; it was confirmed that if TGF-β1 was not added, a differentiation rate was not affected). Nine days after seeding (up to 25 days after seeding, the same result was obtained), the cells were collected by pipetting.

(6) Iba1 Immunostaining

The cells collected by the method described in (5) were seeded in a PDL/laminin-coated plate (Biocoat; manufactured by Corning). The next day, the adhered cells were fixed at 4° C. for 1 hour using 4% paraformaldehyde (PFA)/PBS. The fixed cells were washed 3 times with PBS, treated with 0.1% Triton X-100/PBS for 5 minutes, washed 3 times with PBS, and then treated with a blocking solution (1.5% donkey serum/PBS) for 30 minutes. Next, the cells were reacted with 1/50 anti-Iba1 antibody (manufactured by Abcam)/the blocking solution at 4° C. overnight, washed 3 times with PBS, and then reacted with 1/500 AlexaFluor 488 donkey anti-goat IgG (H+L)+1/10,000 Hoechst 33342 (manufactured by Invitrogen)/the blocking solution for 90 minutes. Finally, the cells were washed 3 times with PBS, and then observed using a fluorescence microscope.

An image taken under a fluorescence microscope is shown in FIG. 1. All (100%) of the cells collected were Iba1-positive and had elongated projections (FIG. 2). These results show that the cells differentiated from hiPS cells by the method of the present application were microglia.

Example 2 Production of Microglia Using Feeder-Free iPS Cell (1) Maintaining and Culturing of Feeder-Free iPS Cell Cell line TkDA3-4 purchased from Tokyo University Stem Cell Bank was used. For coating, iMatrix-511 (manufactured by nippi) was used. As a dissociation solution, 0.5× Triple select [a 2:1:1 mixture of Triple TM select CTS (manufactured by Invitrogen) and 0.5 mol/l of EDTA pH 8.0 (manufactured by NacalaiTesque) and PBS (manufactured by Wako)] was used. As a medium, AK03N (manufactured by Ajinomoto) was used.

(2) Differentiation Induction

Step 1

A 6-well cell adhesion plate attaching iPS cells that had been subcultured by the method described in (1) was washed with PBS, and then treated with 1 ml/well of ReLeSR (manufactured by STEM CELL Technologies) at 37° C. for 10 minutes. The plate was washed with PBS again. After adding 10 ml of differentiation medium D, the hiPS cells were scraped with a cell scraper. The hiPS cells thus obtained were seeded at a density of about 1/10 (the cells in 1 well of the 6 well plate were seeded on two 10 cm dishes) on the 10T1/2 cells that had been subcultured by the method described in Example 1(3), together with 20 ng/ml of VEGF (manufactured by PEPROTECH; according to Non-patent Literature 4, it is not necessary to add VEGF). After 3, 6, 8, 10 and 12 days from seeding, the medium was exchanged with differentiation medium E supplemented with 20 ng/ml of VEGF (manufactured by PEPROTECH; according to Non-patent Literature 4, it is not necessary to add VEGF). On day 13, the cells were collected. The cells were scraped from the cell culture dish with a cell scraper while Sac was destroyed, and then the cells were collected through a cell strainer (40Φ). After centrifugation [120G (it was confirmed that centrifugation at 100-150G did not affect a recovery rate and purity), 10 minutes, no brake], a pellet was resuspended in differentiation medium E.

Step 2

To the all cells obtained by step 1 were added IL-3 (50 ng/ml; manufactured by PEPROTECH) and GM-CSF (50 ng/ml; manufactured by PEPROTECH), and resuspension of 5 cell culture dishes was seeded on 10T1/2 in one cell culture dish. After 3 days, 5 ml of differentiation medium E containing IL-3 and GM-CSF was added to the cells. After 6 days, the cells were collected by pipetting.

Step 3

The primitive monocytes obtained by step 2 were resuspended in medium F for co-culturing. To the suspension were added 50 ng/ml of M-CSF (manufactured by PEPROTECH) and 50 ng/ml of IL-34 (manufactured by PEPROTECH), and the cells were seeded at a density of 1/2 on the primary cultured rat astrocytes described in Example 1(4). Two days after seeding, 5 ml of blood cell differentiation medium F supplemented with M-CSF and IL-34 was added. On day 4 and day 7, 7 ml of the medium was collected and centrifuged (300 G, 3 minutes). A pellet was resuspended in 8 ml of blood cell differentiation medium F supplemented with M-CSF, IL-34, and 50 ng/ml of TGF-β1 (manufactured by PEPROTECH; it was confirmed that if TGF-β1 was not added, a differentiation rate was not affected). Nine days after seeding, the cells were collected by pipetting.

(3) Iba1 Immunostaining

The cells collected by step 3 were seeded in a PDL/laminin-coated plate (Biocoat; manufactured by Corning). The next day, the adhered cells were fixed at 4° C. for 1 hour using 4% paraformaldehyde (PFA)/PBS. The fixed cells were washed 3 times with PBS, treated with 0.1% Triton X-100/PBS for 5 minutes, washed 3 times with PBS, and then treated with a blocking solution (1.5% donkey serum/PBS) for 30 minutes. Next, the cells were reacted with 1/50 anti-Iba1 antibody (manufactured by Abcam)/the blocking solution at 4° C. overnight, washed 3 times with PBS, and then reacted with 1/500 AlexaFluor 488 donkey anti-goat IgG (H+L)+1/10,000 Hoechst 33342 (manufactured by Invitrogen)/the blocking solution for 90 minutes. Finally, the cells were washed 3 times with PBS, and then observed using a fluorescence microscope. As a result, all (100%) of the cells collected were Iba1-positive and had elongated projections. These results show that the cells differentiated from feeder-free hiPS cells by the method of the present disclosure were microglia.

Example 3 Study of Differentiation Induction Period at Blood Progenitor Cell Production Stage (1) Differentiation Induction Step 1

A 10 cm cell culture dish attaching hiPS cells that had been subcultured by the method described in Example 1(2) was washed with PBS. To the dish was added 1.5 ml of Dissociation Solution (manufactured by ReproCELL) to dissociate MEF while the dish was swung. The dissociated MEF was aspirated with an aspirator, and further washed with PBS. After adding 10 ml of differentiation medium D, the hiPS cells were scraped with a cell scraper. The hiPS cells thus obtained were seeded at a density of 1/40 (the cells on one dish were seeded on about 40 dishes) on the 10T1/2 cells that had been subcultured by the method described in Example 1(3), together with 20 ng/ml of VEGF (manufactured by PEPROTECH; according to Non-patent Literature 4, it is not necessary to add VEGF). After 3, 6, 8, 10 and 12 days from seeding, the medium was exchanged with differentiation medium E supplemented with 20 ng/ml of VEGF (manufactured by PEPROTECH; according to Non-patent Literature 4, it is not necessary to add VEGF). After culturing for predetermined days, the cells were collected. The cells were scraped from the cell culture dish with a cell scraper while Sac was destroyed, and then the cells were collected through a cell strainer (40Φ). After centrifugation [120G (it was confirmed that centrifugation at 100-150G did not affect a recovery rate and purity), 10 minutes, no brake], a pellet was resuspended in differentiation medium E.

Step 2 to Step 3

They were performed in the same manner as step 2 to step 3 in Example 2.

(2) Iba1 Immunostaining

The Iba1 immunostaining was performed in the same manner as Example 2(3).

A period for producing blood progenitor cells was set as a period of 6, 13, 20 or 27 days. When differentiation induction into microglia was performed in the above-mentioned periods, microglia were produced under the all conditions. Particularly, differentiation induction efficiency into microglia was better in a period of 13 to 27 days.

Example 4 Study of Differentiation Induction Period at Primitive Monocyte Production Stage (1) Differentiation Induction Step 1

A 10 cm cell culture dish attaching hiPS cells that had been subcultured by the method described in Example 1(2) was washed with PBS. To the dish was added 1.5 ml of Dissociation Solution (manufactured by ReproCELL) to dissociate MEF while the dish was swung. The dissociated MEF was aspirated with an aspirator, and further washed with PBS. After adding 10 ml of differentiation medium D, the hiPS cells were scraped with a cell scraper. The hiPS cells thus obtained were seeded at a density of 1/40 (the cells on one dish were seeded on about 40 dishes) on the 10T1/2 cells that had been subcultured by the method described in Example 1(3), together with 20 ng/ml of VEGF (manufactured by PEPROTECH; according to Non-patent Literature 4, it is not necessary to add VEGF). After 3, 6, 8, 10 and 12 days from seeding, the medium was exchanged with differentiation medium E supplemented with 20 ng/ml of VEGF (manufactured by PEPROTECH; according to Non-patent Literature 4, it is not necessary to add VEGF). On day 13, the cells were collected. The cells were scraped from the cell culture dish with a cell scraper while Sac was destroyed, and then the cells were collected through a cell strainer (40Φ). After centrifugation [120G (it was confirmed that centrifugation at 100-150G did not affect a recovery rate and purity), 10 minutes, no brake], a pellet was resuspended in differentiation medium E.

Step 2

To the all cells obtained by step 1 were added IL-3 (50 ng/ml; manufactured by PEPROTECH) and GM-CSF (50 ng/ml; manufactured by PEPROTECH), and resuspension of 5 cell culture dishes was seeded on 10T1/2 in one cell culture dish. After 3 days, 5 ml of differentiation medium E containing IL-3 and GM-CSF was added to the cells. After culturing for predetermined days, the cells were collected by pipetting. The cell suspension thus obtained was centrifuged (300G, 3 minutes). A pellet was subjected to the next step.

Step 3

The monocytes obtained by step 2 were resuspended in medium F for co-culturing. To the suspension were added M-CSF (50 ng/ml; manufactured by PEPROTECH) and IL-34 (50 ng/ml; manufactured by PEPROTECH), and the cells were seeded at a density of ½ on the primary cultured rat astrocytes described in Example 1(4). Two days after seeding, 5 ml of medium F supplemented with M-CSF and IL-34 was added. On day 4 and day 7, 7 ml of the medium was collected and centrifuged (300 G, 3 minutes). A pellet was resuspended in 8 ml of medium F supplemented with M-CSF, IL-34, and TGF-β1 (50 ng/ml; manufactured by PEPROTECH; it was confirmed that if TGF-β1 was not added, a differentiation rate was not affected). Nine days after seeding, the cells were collected by pipetting.

(2) Iba1 Immunostaining

The Iba1 immunostaining was performed in the same manner as Example 2(3).

Experiments were performed using monocyte induction periods of 0 (an experiment where step 2 was skipped was expedientially regarded as 0 day), 1, 6, 10, 13, 17 and 20 days. In the all experiments using the above-mentioned induction periods, microglia were efficiently produced.

Example 5 Study of Cytokine Concentration (1) Differentiation Induction
Step 1
Blood progenitor cells were produced in the same manner as step 1 in Example 4.
Step 2
To the all cells obtained by step 1 were added predetermined concentration of IL-3 (manufactured by PEPROTECH) and predetermined concentration of GM-CSF (manufactured by PEPROTECH), and resuspension of 5 cell culture dishes was seeded on 10T1/2 in one cell culture dish. After 3 days, 5 ml of differentiation medium E containing IL-3 and GM-CSF was added to the cells. After culturing for 6 days, the cells were collected by pipetting. The cell suspension thus obtained was centrifuged (300G, 3 minutes). A pellet was subjected to the next step.
Step 3
The monocytes obtained by step 2 were resuspended in medium F for co-culturing. To the suspension were added predetermined concentration of M-CSF (manufactured by PEPROTECH) and predetermined concentration of IL-34 (manufactured by PEPROTECH), and the cells were seeded at a density of ½ on the primary cultured rat astrocytes described in Example 1(4). Two days after seeding, 5 ml of medium F supplemented with M-CSF and IL-34 at the same concentration as at the time of cell seeding was added. On day 4 and day 7, 7 ml of the medium was collected and centrifuged (300 G, 3 minutes). A pellet was resuspended in 8 ml of medium F supplemented with M-CSF and IL-34 at the same concentration as at the time of cell seeding, and TGF-β1 (manufactured by PEPROTECH). Nine days after seeding, the cells were collected by pipetting.

(2) Iba1 Immunostaining
The Iba1 immunostaining was performed in the same manner as Example 2(3). Results are summarized in FIG. 3. Based on the results of Example 1, an equivalent differentiation induction efficiency is shown as "○", and a 1/10 or less differentiation induction efficiency is shown as "Δ".

Experiments were performed using 0, 25, 50, and 100 ng/ml of each cytokine. Under the all conditions, microglia were produced. When 25 ng/ml or more of IL-3 or ng/ml or more of GM-CSF was added in step 2, the differentiation induction efficiency was particularly increased. When 25 ng/ml or more of M-CSF was added in step 3, the efficiency was particularly increased.

INDUSTRIAL APPLICABILITY

According to the method of the present invention, microglia can be efficiently produced from pluripotent stem cells. The microglia thus obtained can be used for various basic studies including study of microglia itself and study for diseases that microglia is involved in. Further, the microglia is extremely useful in a method for screening therapeutic agents for diseases that microglia is involved in which comprises using microglia, or in selecting so-called tailor-made therapeutic agents, in which therapeutic agents best suited to patients are selected by using microglia prepared from pluripotent stem cells established from the individual patients. Application of the microglia to cell therapy is also expected.

The invention claimed is:

1. A method for producing microglia from a pluripotent stem cell, the method comprising the following steps:
    (a) a step of co-culturing a pluripotent stem cell with a feeder cell for 7 days or more to obtain a blood progenitor cell,
    (b) a step of co-culturing the blood progenitor cell obtained by step (a) with a feeder cell in the presence of IL-3 and/or GM-CSF to obtain a primitive monocyte, and
    (c) a step of co-culturing the primitive monocyte obtained by step (b) with an astrocyte in the presence of M-CSF, or culturing the primitive monocyte obtained by step (b) using an astrocyte supernatant in the presence of M-CSF.

2. The method according to claim 1, wherein the culturing period of step (a) is for 13 days or more.

3. The method according to claim 1, wherein the co-culturing or culturing of step (c) occurs in the presence of IL-34.

4. The method according to claim 1, wherein the co-culturing of step (b) occurs in the presence of IL-3 and GM-CSF.

5. The method according to claim 1, wherein the feeder cell is a 10T1/2 cell or OP9 cell.

6. The method according to claim 1, wherein the co-culturing of step (a) occurs in the presence of VEGF.

7. The method according to claim 1, wherein the pluripotent stem cell is an iPS cell.

8. The method according to claim 7, wherein the iPS cell is obtained from human or mouse.

* * * * *